United States Patent [19]
Porges
[11] Patent Number: 4,559,053
[45] Date of Patent: Dec. 17, 1985

[54] BAGS FOR MEDICAL USE AND INTENDED IN PARTICULAR FOR PARENTERAL NUTRITION

[75] Inventor: Etienne Porges, Neuilly, France
[73] Assignee: Synthelabo, Paris, France

[21] Appl. No.: 522,669
[22] Filed: Aug. 12, 1983

[30] Foreign Application Priority Data
Sep. 2, 1982 [FR] France ................................ 82 15008

[51] Int. Cl.[4] ......................... A61M 5/00; B65D 35/07
[52] U.S. Cl. ..................................... 604/408; 206/463; 222/143; 604/410; 215/1 C
[58] Field of Search ................. 150/55, 8, 9; 206/466; 383/2, 9, 105-113, 119, 38, 58, 67; 604/415, 403, 408-412, 317, 322-326; 222/92-98; 128/760-768

[56] References Cited

U.S. PATENT DOCUMENTS 1,494,950 11/1921 Clark .
2,950,029 10/1956 Winstead ............................ 215/1 C
3,028,863 4/1962 Mattson ................................ 604/410
3,278,109 10/1966 Salway .................................. 383/67
3,342,326 10/1967 Zackheim ............................ 206/56
3,520,471 10/1968 Faust ..................................... 229/56
3,715,074 2/1973 Michel ................................ 604/408
3,740,770 6/1973 Villari ..................................... 4/110
3,788,369 1/1974 Killinger ............................ 141/114
4,072,233 2/1978 Kramer et al. ...................... 206/634
4,191,231 3/1980 Winchell et al. ................... 604/408
4,248,223 2/1981 Turner et al. ....................... 604/133
4,411,364 10/1983 Friedman ........................... 206/466

*Primary Examiner*—Stephen C. Pellegrino
*Assistant Examiner*—Karen Kaechele
*Attorney, Agent, or Firm*—Wegner & Bretschneider

[57] ABSTRACT

A bag intended to contain injectable products has two sides, each constituted by a sheet of a complex film and formed so as to have a flat-bottomed, dish-shaped part. At the flat rim of this part, each film sheet is welded to one of the flat surfaces of the semi-rigid reinforcing frame so that the two dish-shaped parts are fitted within each other. Connecting tubes traverse one side of the frame and open out in the central opening of the latter between the two sheets.

18 Claims, 2 Drawing Figures

BAGS FOR MEDICAL USE AND INTENDED IN PARTICULAR FOR PARENTERAL NUTRITION

Figure 1:
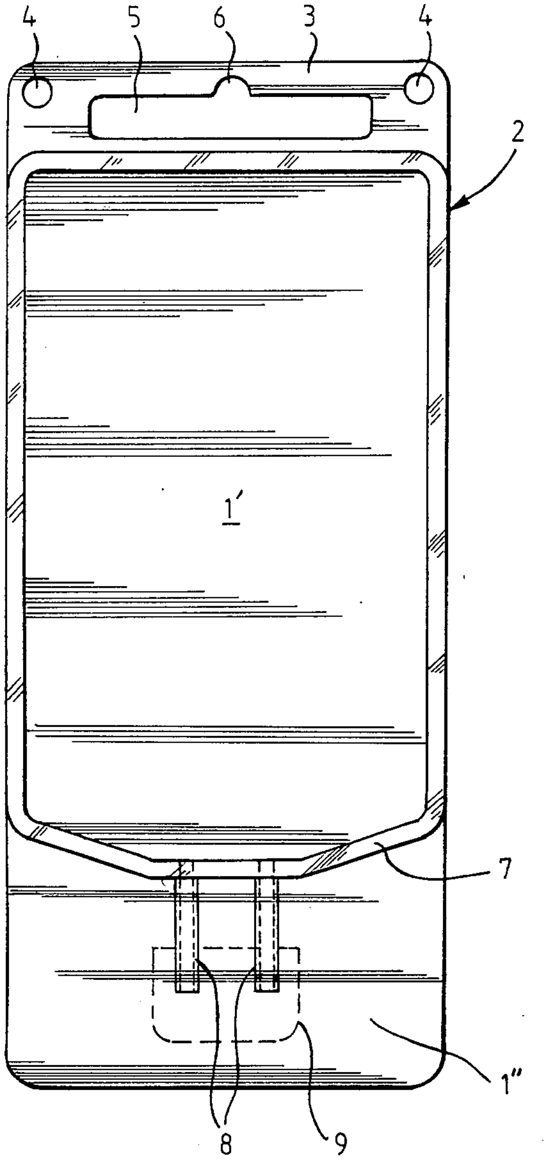

The present invention concerns bags for medical use and relates more particularly to bags intended for parenteral nutrition.

Parenteral nutrition is a mode of artificial nutrition which consists of supplying a patient, who can no longer take food entirely or partly by using the physiological digestive tract, intravenously with all the elements necessary for his nutrition. When complete parenteral nutrition is required, it is desirable to combine the three types of nutrients in a rational manner: glucides, most frequently in the form of glucose, protides in the form of balanced mixtures of amino acids, lipids as well as additives such as electrolytes, oligoelements and vitamins which take the form of emulsions, aqueous solutions and aqueous suspensions which may be injected.

Unfortunately, in mass production, the association of glucose and amino acids within the same aqueous medium is difficult because of Maillard's reaction. According to this reaction, the combination of reducing sugars with amino acids leads to the formation of new organic compounds whose colouring varies from yellow to dark brown and this reaction has other drawbacks, in particular, the emergence of active compounds or those not amenable to metabolism, even toxic ones and above all, a modification of the nutritive value of the mixture. For these reasons, the nutritive mixture is generally prepared extemporaneously or within 24 hours before being administered to the patient.

To effect this preparation, a set-up has been used for a long time comprising a small glass bottle filled with amino acids and bottled under vacuum, a larger sized bottle partly filled with glucose and vacuum bottled, and also a connecting tube provided at one end with a perforator and an incorporated dose of air and at the other end, with a perforating needle. By means of this connecting tube and its perforators, the operator effects the transfer of the amino acids from the small bottle into the glucose contained in the large bottle, thanks to the vacuum obtaining in the latter. Experience has shown that errors in manipulation are relatively frequent, that the handling of the bottles is not effected under proper aseptic conditions, and that a considerable portion of the amino acids was not being transferred into the glucose so that it is necessary to add a dose of air to the bottle to be emptied. Moreover, these glass bottles have the disadvatages of being inconvenient to store and difficult to convey.

For these reasons, the attempt has recently been made to replace these glass bottles by bags made of a pliable material.

The reusable bags made of a silicone elastomer which were earlier substituted for glass bottles, have recently been replaced by disposable plastic bags, most frequently made of polyvinyl chloride or polyethylene polyvinyl acetate, taking the development of bags commonly used for perfusions as an example.

Such a bag is most frequently formed by two rectangular sheets made of plastic material, flat welded to each other on four sides so as to define between the two sheets and the four welded sides, a reservoir whose volume is zero before it is filled under pressure. On one of the sides of the two rectangular sheets a reinforcing element, also made of a plastic material, is inserted between the two facing sides of the two sheets and welded to the latter and this reinforcing element has holes wherewith it is possible to hang up or fasten the bag. On the opposite side of the rectangular sheets, one or several connecting tubes are introduced between the two sheets and welded to the latter in a leak proof manner so as to allow the filling or emptying of the bag as well as the extemporaneous addition of a medication in addition to the nutrient mixture possibly contained in this bag. A bag of this type is described in U.S. Pat. No. 3,788,369 and FR No. 2,431,289 and bags of a closely related structure are described in U.S. Pat. Nos. 3,740,770 and 3,342,326.

Taking the make up of such a bag into account, when filling it with any liquid it is necessary to exert a considerable pressure which may attain 100 kPa in order to deform the rectangular bag and in order to draw out the two plastic sheets which form its two sides. When the bag is filled, it assumes the shape of a small cushion and because of the stresses exerted on the sheets of plastic material which are constantly kept under tensile stress, the welds joining the sheets together or joining the sheets to the connecting tubes are subjected to considerable stresses and this entails a risk of leakage. Moreover, the bag is liable to permanent deformations, and the fact that it is necessary to keep under pressure, from the time of its filling to the time of its use, a bag which is fragile and may be easily damaged because of the stresses exerted in the sheets constitutes a major drawback.

Moreover since the materials commonly used for making such bags such as polyvinyl chloride and polyethylene polyvinyl acetate, are not impervious to atmospheric gases and steam and since it is indispensable to obtain a bag having good mechanical strength characteristics, the sheets of the plastic material used have a relatively considerable thickness which is generally comprises between 300 and 400 microns. The making of these bags therefore entails a considerable consumption of plastic materials and, in their application to parenteral nutrition, the nutrient mixtures must be prepared in these bags extemporaneously or shortly before being administered to the patient since, as has already been stated and in contrast to the liquids commonly used for perfusions, the parenteral nutrition mixtures are subject to ready deterioration and the amino acids which they comprise, are easily exposed to oxidation by the oxygen of the air.

It should also be noted that certain plastic materials used for making these bags which are satisfactorily used as physiological serum bags, for perfusion or transfusion liquids or as bags for vesical irrigation, are not suitable for making bags for storing injectable substances intended for parenteral nutrition because some of their constituents, in particular plasticizer agents, are extracted from the coating layers of the plastic material on contact with these injectable products and move into these latter thereby polluting them.

For these various reasons, these bags are used, in their application to parenteral nutrition, as means for administering a nutrient mixture prepared extemporaneously and not as means for storing a "ready for use" nutrient mixture prepared industrially and also transported in its bag.

With the present invention, it is proposed to remedy these various disadvantages. It is an object of the invention to provide a bag having a volume which is practically zero when empty, and is hence easy to store, but which can be filled without it being necessary to exert any notable pressure on its sides and hence on the welds so that the bag is less fragile to carry in its filled state.

It is also an object of the invention to provide a bag which has adequate mechanical strength although the sheets of the plastic material used for making of its sides are a great deal thinner than in the prior art.

Another object of the invention is to make a bag not having any sealing problems at the level of the passing of the connecting tubes.

Finally it is a further object of the invention to make on a mass production scale, ready for use bags, prepared and filled with nutrient mixtures, intended for parenteral nutrition, whereby it is possible to store and carry these mixtures in the bags, these bags finally being also capable of being used as means of administration.

Accordingly the present invention provides a bag intended to contain injectable products said bag having: two sides each constituted by a pliable sheet comprising at least one layer of plastic material; and a semi-rigid reinforcing frame of a plastic material with flat surfaces wherein each of the sheets is formed with a dished shape and has the parts of the sheet which surround the concave part of each dish formation fixed in a leakproof manner on either side of the frame, each one on a respective one of the two flat surfaces of the frame so that when the bag is empty the sheets interfit one in the other on the same side of the plane of symmetry passing through the thickness of the frame so as to delimit between the two sheets and within at least one opening of the frame a compartment with a variable volume which is practically zero when the bag is empty.

The bag has good mechanical strength as well as a considerable volume which can be filled before the sides of the bag are subjected to any substantial tensile stress.

From U.S. Pat. No. 1,494,950, there is known a container comprising two sides constituted by pliable sheets of linen or fabric based paper, each joined to one of two flat sides of a semi-rigid frame of cardboard, but such a container is unsuitable for the applications aimed at in the patent application.

Advantageously, in order to avoid any sealing problem where the connecting tubes pass into the bag, these tubes, which open on the one hand outside the bag and on the other hand within the bag between the two sheets of the latter, pass through the thickness of one side of the frame and are preferably extended towards the outside of the frame by end fittings.

So as to have rigorously flat sides and to be integral with the end fittings of these connecting tubes, the frame of a bag in accordance with the invention is advantageously obtained from a single piece by pressure injection moulding.

Preferably, the two sheets of a bag each have at least one portion which extends beyond at least one side of the frame traversed by at least one connecting tube and which defines with the corresponding part of the other sheet and to which it is preferably joined, a subsidiary bag for the protection of the connecting tubes and possibly of the end fittings of these latter. Thus it is essential to open the subsidiary protection bag either (a) by tearing it, possibly at the level of the portion of lesser strength provided for this purpose, or (b) by cutting it in order to gain access to the connecting tubes.

In one embodiment intended to constitute a bag for the storage, carriage and administration of an injectable mixture, the bag in accordance with the invention comprises at least two connecting tubes, one of which is permanently closed after the bag has been filled.

Preferably also, one of the sides of the frame which is not traversed by the connecting tubes has at least one opening for the fastening and/or hanging up of the bag, and/or at least one fastening device and/or a suspension device for the bag.

In one particular form of embodiment intended for parenteral nutrition, each sheet of the bag is constituted by a complex film of thin layered materials, comprising at least one layer constituting a barrier impervious to atmospheric gases and to steam, for instance made of polyvinylidene chloride sandwiched between at least two layers, at least one of which, situated towards the interior of the bag, is made of a material compatible with the contents of the bag and does not contain any noxious, toxic or plasticizer agents which could be extracted by this content, for instance, of polyethylene polyvinylacetate.

The combination constituted by these three layers may itself be sandwiched between two layers of a plastic material, for instance of polyethylene.

It is also possible for each laminated film constituting one of the sheets of the bag to comprise at least one thin metal layer, for instance of aluminium.

In order to reduce the leakage risks at the welds at the sides of the bag against the reinforcing frame, this latter is preferably made of the same plastic material as the layer of the complex film with which it comes into contact via its flat sides.

Finally, it is possible to make a multiple bag by using a frame having several openings wherewith the sheets define several compartments of a variable volume.

Figure 2:
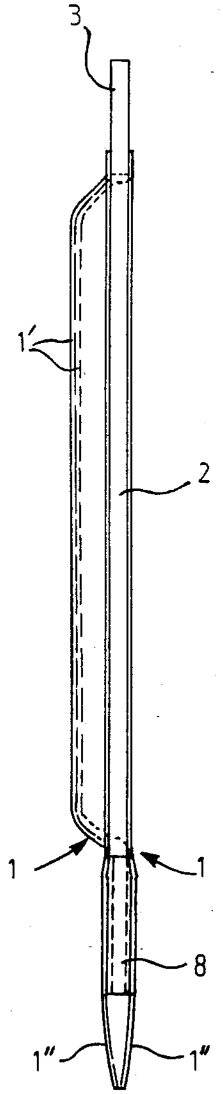

The present invention will be more readily understood with the help of a particular embodiment which will be described below on a non-restrictive basis with reference to the attached Figures wherein:

FIG. 1 is a front view, partly in cross section at the level of the connecting tubes, of an empty bag in accordance with the invention; and FIG. 2 is a side view, also in cross section at the level of the connecting tubes, of the bag represented in FIG. 1.

The bag represented in FIGS. 1 and 2 comprises two transparent sheets 1, each formed by a laminated film of thin layers of plastic materials. This laminated film, which always comprises at least one layer constituting a barrier which is impervious to atmospheric gases and to moisture, comprises in a first embodiment a central layer of polyvinylidene chloride sandwiched between two polyethylene polyvinylacetate layers. This three layer combination wherein the central polyvinylidene chloride layer constitutes the impervious barrier, may itself be sandwiched between two layers of another plastic material, for instance polyethylene or any other plastic material compatible with the contents of the bag and not containing any plasticizer agents as does polyvinyl chloride, nor noxious or toxic ingredients which could be extracted by the contents of the bag. The laminated films from which sheets 1 are cut do not necessarily have a symmetrical structure and this structure can comprise a greater or smaller number of plastic materials in thin layers not only but also a thin metal layer, for instance a layer of aluminium which will not be disposed on one of the outer faces of the laminated film.

The two pliable sheets 1 constituting the surfaces of the bag each have initially a flat and rectangular shape. On the greater part of their surfaces, each of these two sheets 1 is shaped and dished by thermo-forming so that it substantially has the shape of a flat bottomed dish 1', surrounded by a flat edge and is adjacent along one part of this edge to the undeformed part 1" sheet 1. The depth of the flat bottomed dish 1' is limited to a few centimeters and is chosen according to the final volume of the bag that one wishes to obtain.

The bag also comprises a semi-rigid reinforcing frame 2 whose two side surfaces are flat and which has a single central opening whose shape in plan corresponds substantially to that of the flat bottomed dished part 1' of each sheet 1. Viewed in plan, the width of the flat face of frame 2 surrounding its central opening is substantially equal to that of the flat rim of each sheet 1 surrounding the flat-bottomed dish-shaped portion 1' of the latter, except at the level of an enlarged end 3 of the frame 2. This enlarged end 3 has two circular lateral holes 4 intended to allow frame 2 to be hung up and fastened to a support, or to allow suspension and fastening devices for the frame 2 to pass through to a support, as well as an elongated central perforation 5 defining a handle for the user to hold and carry it and which has a central notch 6 on the opposite side from the opening of the frame, also to allow frame 2 to be fastened when hung up either directly or by means of a fastening device. If desired, the frame 2 may alternatively or additionally include means for fastening the bag to a suspension support. Frame 2 has, on its side 7, at the opposite end from the enlarged end 3, two connecting tubes formed by tubular end fittings 8 projecting in relation to side 7 towards the outside of frame 2 in a direction away from the central opening of the frame and the axial ducts of the end fittings 8 extend within the thickness of side 7 and open out in the central opening of frame 2.

To ensure the proper flatness of the two surfaces of frame 2, and to obtain this frame 2 integrally with its enlarged end 3 having holes 4 and 5 and the end fittings 8, the frame 2 is made by pressure injection moulding of a plastic material which is the same as that of the surface layers of the complex films of sheets 1 with which frame 2 comes into contact when the bag is assembled.

This assembly is obtained by pressure welding of the flat rim of each of sheets 1 which surrounds the flat-bottomed dish-shaped part 1' against one of the flat surfaces of frame 2 around the central opening of the latter so that the two sheets 1 are joined in a leak proof manner to frame 2 on either side of the frame. Moreover, sheets 1 are welded to the frame 2 in an asymmetrical manner by being disposed in such a way that the two concave substantially flat-bottomed dish-shaped parts 1' are fitted within each other as has been clearly shown in FIG. 2. In register with the opening of frame 2, the sheets 1 are therefore not disposed symmetrically, one with respect to the other in relation to the plane of symmetry passing through the thickness of frame 2, but on one and the same side of this plane of symmetry and when not in use, the bag therefore has a volume which is practically zero.

Thus, when being filled, the dish-shaped part 1' which, when not in use, is accommodated in the other part of the same shape, comes to take up on the other side of frame 2 a symmetrical position to that which it occupied in relation to the plane of symmetry of frame 2.

Thanks to this deformation and the presence of frame 2 between the two sheets 1, the bag has a considerable volume, of the order of 40% of its maximum volume which can be filled without exerting any pressure and without any appreciable stress being applied to the sheets 1 and hence on their welds. This considerably reduces the risk of rupturing of the sheets 1 and the welds of these sheets to the frame 2. The filling of the bag may then be completed to its maximum volume by drawing out the sheets, but for an equivalent maximum volume, a bag made in this way is stressed considerably less at the welds and the surface film layers than a bag of the prior art, so that the risks of a permanent deformation and of bursting are reduced.

As the connecting tubes 8 pass through the thickness of frame 2 and open out in the bag between the two sheets 1, any risk of leakage between the films of sheet 1 and of connecting tubes 8 is eliminated.

Moreover, since the suspension or fastening devices of the bag are only connected to the frame 2 via its enlarged end 3, the mechanical strength of the bag is improved since all the pressure stresses are transmitted by the frame 2 to the fastening devices.

For all these reasons, the thickness of the films used to make the sheets 1 may be limited to 100 microns whilst it frequently attains 400 microns in the bags of the prior art.

Moreover, for a given surface area, which is that of the opening in the frame 2, a bag in accordance with FIGS. 1 and 2 offers a far greater volume than that of the bags of the prior art with the same surface in plan. For an equivalent maximum volume, the surface of the frame may therefore be reduced and this also constitutes an advantage inasmuch as the consumption of plastic materials is thereby reduced.

Moreover, the flat parts 1" of the sheets 1 which extend beyond the side wall 7 of the frame 2 traversed by the connecting tubes 8, are welded to each other along their edges and envelope the connecting tubes 8 in a subsidiary protecting bag which when closed acts as a tamper proof device. A flap 9 defined in one of the film parts 1" by a line of lesser mechanical strength, allows this subsidiary bag to be opened by tearing it off to give access to at least one of the connecting tubes 8, for instance the one which is not permanently stoppered after the filling of the bag if the latter is marketed ready for use.

By reason of the make up of the laminated film 1 which ensures a barrier against atmospheric gases and vapour, and the absence of pollution due to the extraction by the contents of the bag of noxious particles from the materials, the bags in accordance with the invention may advantageously be used as bags for parenteral nutrition, by being filled on an industrial scale and then be stored and carried and finally distributed ready for administration to a patient.

Of course, if the reinforcing frame 2 has several openings, it is possible to obtain multiple bags if the sheets of complex film are welded to the frame in such a way that with the frame, they define several compartments with a variable volume.

But, by reason of their structure and the good mechanical properties that they possess, these bags may also be used as bags for blood, for vesical irrigation liquids, for perfusion, for transfusion etc.

I claim:

1. A bag for containing injectable products, comprising:

first and second sides each formed from a pliable film sheet, each of said film sheets comprisig at least one layer of plastic material;

a semi-rigid reinforcing frame formed from a plastic material, comprising side walls defining at least one central opening passing substantially perpendicular to a first plane passing perpendicular to the thickness of the frame and first and second flat faces surrounding said central opening, opposite each other with respect to said first plane;

said first and second film sheets each being shaped in the form of a flat bottomed dish having a surrounding film part which serves as a rim for the dish;

said surrounding film part of said first film sheet being fixed in a leak-proof manner to the first flat face of the frame and said surrounding film part of said second film sheet being fixed in a leak-proof manner to the second flat face of the frame;

connecting tube means communicating the exterior of the bag with the interior thereof, said connecting tube means passing through one of the side walls of the frame; and the first and second film sheets being shaped and arranged so that when the bag is empty, said first and second sheets fit one in the other on the same side of said first plane so as to define between the two film sheets and within said opening of the frame a compartment having a volume which is variable and is practically zero when the bag is empty.

2. A bag according to claim 1, wherein said first and second film sheets are given their dished form by thermo-forming.

3. A bag according to claim 1, wherein said surrounding film parts are fixed to the faces of the frame by welding.

4. A bag according to claim 1, wherein said connecting tube means includes a terminal portion extending towards the outside of the frame.

5. A bag according to claim 1, wherein said frame is made in a single piece by injection moulding.

6. A bag according to claim 1, wherein the first and second film sheets each have at least one part extending beyond said side wall of the frame, said connecting tube means extends between said extending parts of the sheets and said extending part of the first and second film sheets are welded together at least at the edges thereof to define subsidiary protection means for the connecting tube means.

7. A bag according to claim 1, wherein said connecting tube means comprise at least two connecting tubes, one of which is permanently closed after the filling of the bag.

8. A bag according to claim 1, wherein said frame has first and second opposed ends and said first end includes means defining at least one opening for suspension of the bag.

9. A bag according to claim 1, wherein said frame has first and second opposed ends and said first end includes means for suspending the bag.

10. A bag according to claim 1, wherein each of said first and second film sheets is formed from a multi-layer film comprising at least one barrier layer impervious to atmospheric gases and moisture, sandwiched between at least two further layers of which at least that one situated towards the inside of the bag is made of a material compatible with the intended contents of the bag and does not contain noxious, toxic or plasticizer constituents which can be extracted by the intended contents.

11. A bag according to claim 10, wherein said barrier layer is polyvinylidene chloride.

12. A bag according to claim 10, wherein said further layers are both formed of polyethylene polyvinyl acetate.

13. A bag according to claim 10, wherein the combination of said barrier layer and said two further layers is itself sandwiched between two additional layers of plastic material.

14. A bag according to claim 13, wherein said additional layers are both of polyethylene.

15. A bag according to claim 10, wherein each multi-layer film comprises at least one thin metal layer.

16. A bag according to claim 15, wherein said metal is aluminum.

17. A bag according to claim 10, wherein said frame is made of the same plastic material as the contiguous layer of the multi-layer film with which its flat faces come into contact.

18. A bag for containing injectable products, comprising:

first and second sides each formed from a pliable film sheet, each of said film sheets comprising at least one layer of plastic material;

a semi-rigid reinforcing frame formed from a plastic material, comprising side walls defining a plurality of central openings passing substantially perpendicular to a first plane passing perpendicular to the thickness of the frame and first and second flat faces surrounding said central openings, opposite each other with respect to said first plane;

said first and second film sheets each being shaped in the form of a flat bottomed dish having a surrounding film part which serves as a rim for the dish;

said surrounding film part of said first film sheet being fixed in a leak proof manner to the first flat face of the frame and said surrounding film part of said second film sheet being fixed in a leak-proof manner to the second flat face of the frame;

connecting tube means communicating the exterior of the bag with the interior thereof, said connecting tube means passing through one of the side walls of the frame; and the first and second film sheets being shaped and arranged so that when the bag is empty, said first and second sheets fit one in the other on the same side of said first plane so as to define between the two film sheets and said side walls, within said openings of the frame, a plurality of separate compartments having a volume which is variable and is practically zero when the bag is empty.

* * * * *